United States Patent
Zychek et al.

(10) Patent No.: US 7,186,108 B2
(45) Date of Patent: Mar. 6, 2007

(54) CURING UNIT FOR DENTAL MATERIALS

(75) Inventors: George Zychek, Stratford, CT (US); Daniel P. Clark, Stamford, CT (US)

(73) Assignee: Pentron Laboratory Technologies, LLC, Wallingford, CT (US)

( * ) Notice: Subject to any disclaimer, the term of this patent is extended or adjusted under 35 U.S.C. 154(b) by 115 days.

(21) Appl. No.: 10/120,934

(22) Filed: Apr. 11, 2002

(65) Prior Publication Data
US 2003/0193119 A1 Oct. 16, 2003

(51) Int. Cl.
*B29C 35/08* (2006.01)
(52) U.S. Cl. .................... 425/174.4; 264/494
(58) Field of Classification Search ............ 425/174.4; 264/494
See application file for complete search history.

(56) References Cited

U.S. PATENT DOCUMENTS

| | | | |
|---|---|---|---|
| 4,309,617 A | 1/1982 | Long | 250/504 H |
| 4,839,521 A | 6/1989 | Oppawsky | 250/453.11 |
| 4,873,446 A | 10/1989 | Kreitmair | 250/492.1 |
| 5,040,964 A | 8/1991 | Oppawsky | 425/135 |
| 5,104,591 A * | 4/1992 | Masuhara et al. | 264/16 |
| 5,169,579 A * | 12/1992 | Marcus et al. | 264/81 |
| 5,248,456 A * | 9/1993 | Evans et al. | 264/401 |
| 5,266,244 A * | 11/1993 | Yabe et al. | 264/482 |
| 5,298,758 A | 3/1994 | Tateosian | 250/492.1 |
| 5,375,187 A | 12/1994 | Ibsen | 392/416 |
| 5,477,054 A | 12/1995 | Tateosian | 250/492.1 |
| 5,514,214 A * | 5/1996 | Joel et al. | 118/52 |
| 5,886,064 A | 3/1999 | Rheinberger | 523/116 |
| 5,958,468 A * | 9/1999 | Kunkel et al. | 425/174.4 |
| 6,200,134 B1 | 3/2001 | Kovac | 433/29 |
| 6,215,093 B1 * | 4/2001 | Meiners et al. | 219/121.61 |
| 6,287,490 B2 | 9/2001 | Rheinberger | 264/17 |
| 6,318,996 B1 | 11/2001 | Melikechi | 433/29 |
| 6,386,865 B1 * | 5/2002 | Suh et al. | 433/27 |
| 6,583,379 B1 * | 6/2003 | Meiners et al. | 219/121.6 |
| 6,843,967 B2 | 1/2005 | Clark | 422/186 |

* cited by examiner

*Primary Examiner*—Yogendra N. Gupta
*Assistant Examiner*—Emmanuel S. Luk
(74) *Attorney, Agent, or Firm*—Ann M. Knab (57) ABSTRACT

A curing apparatus wherein rapid curing is provided by using light, pressure, pressure and light, or purge, pressure and light to cure resinous materials by application of energy from an external source to excite polymerization in a polymerizable system. An air-tight chamber is provided to house the polymerizable dental material. The apparatus provides an automated system for curing the polymerizable material under light and pressure in the same unit. A purge cycle may be included to minimize or eliminate bubbles and provide an oxygen-free atmosphere.

28 Claims, 7 Drawing Sheets

CURING UNIT FOR DENTAL MATERIALS

BACKGROUND OF THE INVENTION

1. Field of the Invention

This invention relates generally to an apparatus for the rapid curing of resinous materials by application of energy from an external source to excite polymerization in a polymerizable system. More specifically, this invention relates to an apparatus for the rapid curing of dental materials by using light, pressure, pressure and light, or purge, pressure and light.

2. Brief Description of the Related Art

Curing, as used herein, is the processing of a plastic or resinous material from a fluid or soft and compliant state to a permanent hard, durable and solid state. Conventionally, this is accomplished both by the elimination of solvents and by chemical changes involving interlinking of molecules commonly known as polymerization of the material. Of the two, polymerization is the more advantageous since it does not commonly involve dimensional changes and usually produces a substantial increase in the strength of the material. Polymerization is usually caused by the addition of activating chemicals (activators), by irradiation with some form of wave energy, either electric or electromagnetic in nature, or by applying heat, or by a combination thereof.

Figure 1:
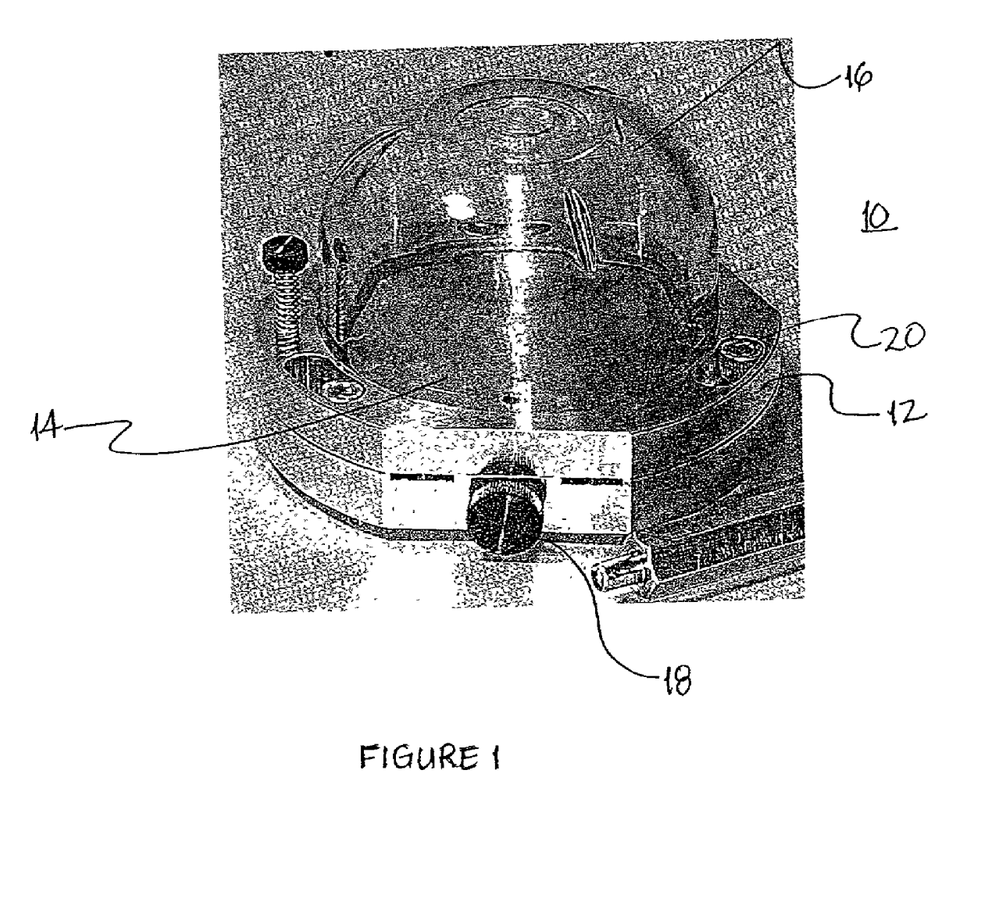
FIG. 1 is a perspective view of a prior art pressure bowl.

The prior art curing processes involve many manual steps that can lead to a variety of errors dependent upon the person performing the operation. One such process uses a pressure bowl depicted in FIG. 1. The pressure bowl 10 includes a base 12 having a platform 14 and a glass or plastic dome or cover 16. A work piece to be treated is placed on platform 14 and glass dome 16 is positioned and locked into place by knob 18. Pressure bowl 10 is then manually connected to an air or gas source at inlet 20. Glass cover 16 is tightened and covered with a cloth to prevent light from entering. Pressure bowl 10 is then pressurized for the required amount of time by turning on the air or gas source. When the process is complete, the air nozzle is removed and pressure bowl 10 is transferred to a light curing box. The work piece, still located in pressure bowl 10, is light cured. After the curing process, pressure bowl 10 is removed from the curing box. To remove the work piece, knob 18 must be turned to unlock glass dome 16. If a glaze is to be placed over the work piece, a purging process is typically required to prevent formation of an oxygen inhibition layer. This involves manually purging bowl 10 with an independent gas source comprising a series of two or more repetitions of filling bowl 10 with gas and releasing and thereafter filling with gas a final time and maintaining gas pressure until the light curing process, as described above, is completed. The manual steps involved in the curing procedures described can lead to many problems in the cured restorations including low strength, distorted shape, tacky surface from incomplete purging, and the like.

There remains a need to simplify the curing process without sacrificing the quality of the final restoration. It is desirable to provide a curing unit that produces consistent results.

SUMMARY OF THE INVENTION

The above-described and other problems and deficiencies of the prior art are overcome or alleviated by the curing apparatus of the present invention, wherein rapid curing is provided by using light, pressure, pressure and light, or purge, pressure and light to cure resinous materials by application of energy from an external source to excite polymerization in a polymerizable system. An air-tight chamber is provided to house the polymerizable dental material.

The apparatus provides an automated system for curing the polymerizable material under light and pressure in the same unit. Pressure eliminates bubbles. A purge cycle may be included to provide an oxygen-free atmosphere and to minimize or eliminate bubbles.

BRIEF DESCRIPTION OF THE DRAWING

For the purpose of illustrating the invention, there are shown in the drawings, features which are presently preferred; it being understood, however that this invention is not limited to the precise arrangements and instrumentalities shown. Referring now to the drawings wherein like elements are numbered alike in the several FIGURES.

DETAILED DESCRIPTION OF THE INVENTION

The present invention is directed to a new and improved curing apparatus for curing a polymerizable resinous material, such as a dental material. U.S. Pat. Nos. 4,873,446, 4,839,521, 5,040, 964, and 4,309,617 are directed to polymerization and/or curing of materials and are hereby incorporated by reference. The dental material may include, but is not limited to at least one filled or unfilled resin having at least one ethylenically unsaturated group. Examples of the ethylenically unsaturated groups include acrylates, methacrylates, vinyl groups and combinations thereof.

Figure 2:
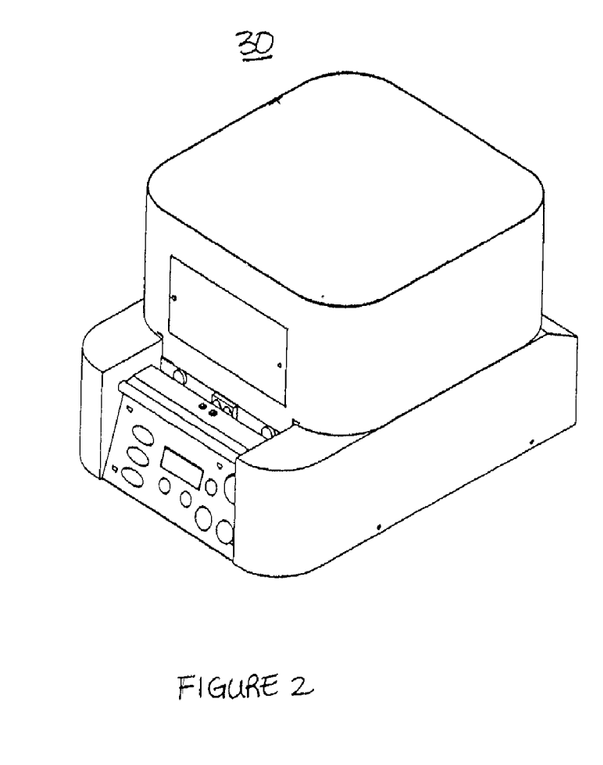
FIG. 2 is a perspective view of the apparatus of the present invention.
Figure 3:
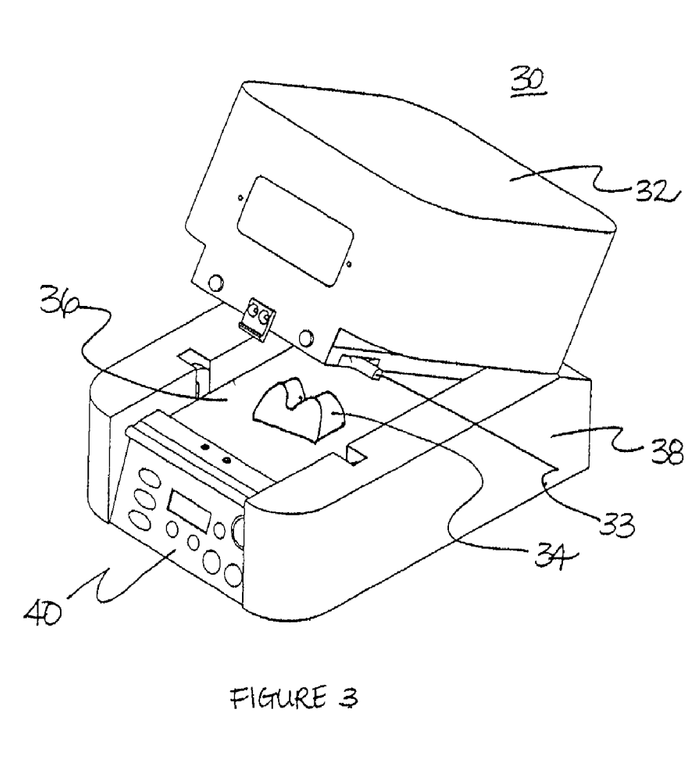
FIG. 3 is a perspective view of the apparatus of FIG. 2 in open position.
Figure 4:
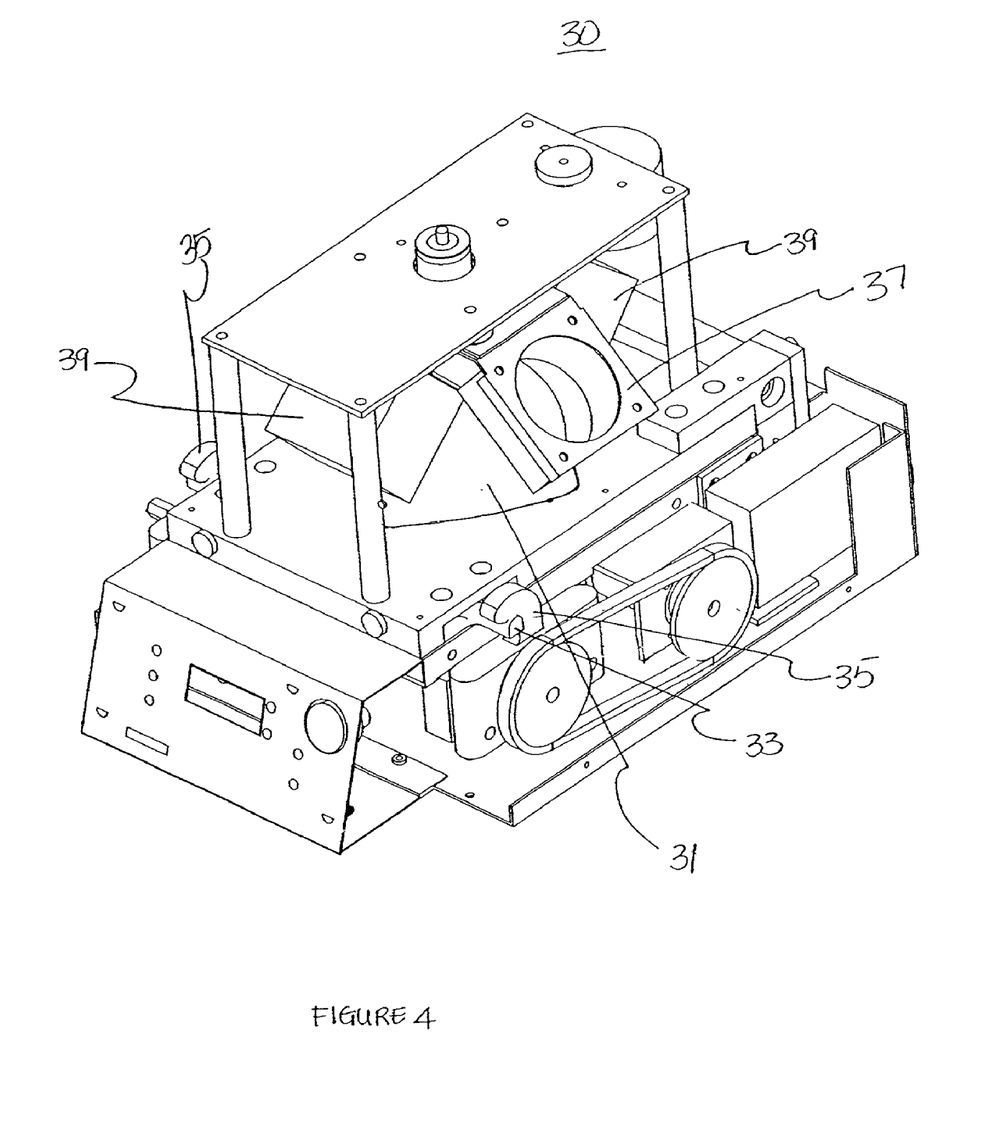
FIG. 4 a perspective view of the apparatus of FIG. 2 showing the internal componentry.
Figure 5:
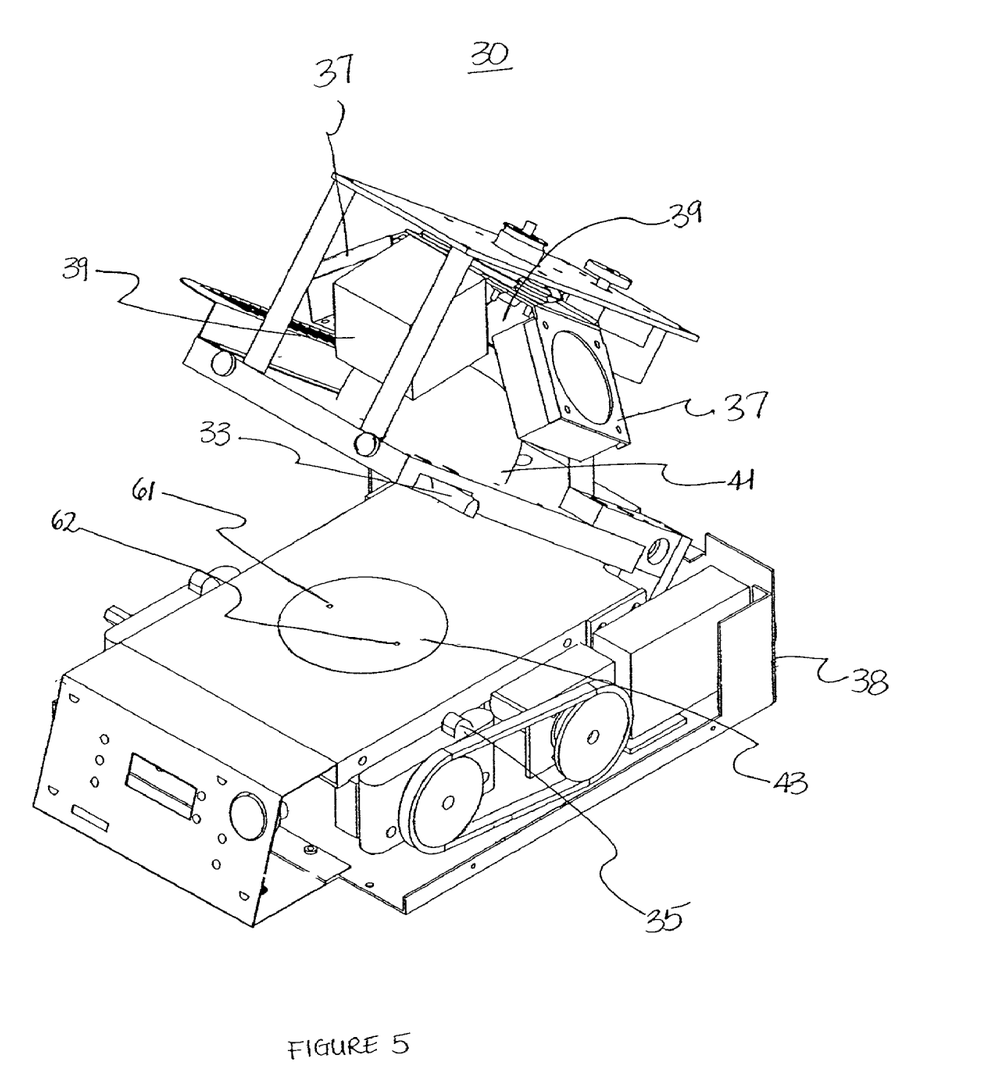
FIG. 5 is a perspective view of the apparatus of FIG. 2 in open position showing the internal componentry.

FIGS. 2 and 3 show curing unit 30 in closed and open position, respectively. FIGS. 4 and 5 show the internal componentry of curing unit 30, in closed and open position, respectively. Curing unit 30 provides a variety of curing options including light alone, pressure alone (does not cure, but can be used to reduce porosity), light and pressure in combination, and a purge cycle to be used with light and pressure.

Curing unit 30 provides a facile method of curing by opening cover 32 and placing a work piece 34 on a platform 36 of base 38. The "light only" mode allows the user to select the time the light is on. The work chamber is closed and opened manually. There is no pressure benefit in this mode. This curing mode provides curing with light only. FIGS. 4 and 5 show the light source comprising two lamps 39 arranged above a transparent dome-shaped cover 41 that is positioned over work area or zone 43 on base 38 which creates an airtight chamber 31 when in closed position. The lamps may comprise light emitting diodes, tungsten, halogen, mercury vapor, short arc xenon, or a metal halide source. The light source may comprise one or a plurality of lamps directed at work area 43. Preferably, the spectral output of the lamp utilized herein is in the range of between about 380 nm to about 550 nm.

Lamps 39 may rotate to provide even curing throughout the material. Cover 32 further may comprise one or more fans 37 to prevent overcuring of the materials. Overcuring tends to make cured composite brittle and less tough. The inclusion of fans 37 aids to control the temperature inside air-tight chamber 31 to below 140° C.

Figure 7:
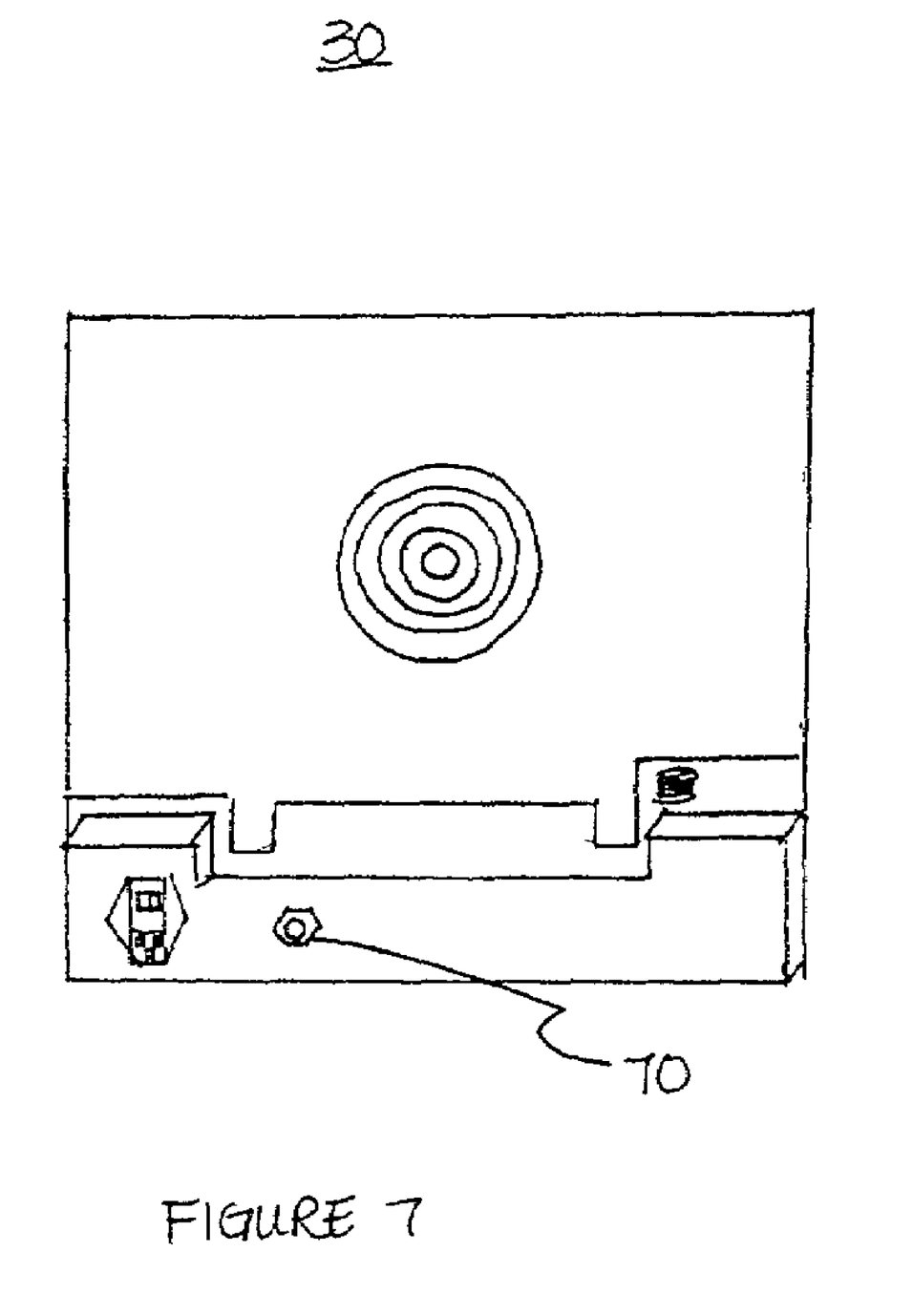
FIG. 7 is a rear plan view of the apparatus shown in FIG. 2.

An inlet 61 and an outlet 62 are located in work area 43 to provide ingress and egress for pressurization. The "pressure/light" mode light cures simultaneously with the application of pressure. The pressure cure is recommended for removal of entrapped bubbles from the composite material. The time allocated for applying pressure inside the work chamber is input or programmed into the curing unit. The time allocated for applying light to the work chamber is input or programmed into the curing unit. After work piece 34 is placed in the curing chamber and the chamber is closed, the pressure chamber is automatically pressure sealed after the start key is pressed. The work is then pressurized for the user-programmed time before the light is turned on. The pressurized atmosphere may include air, nitrogen or any inert gas such as argon, xenon, krypton and the like. The air or gas is supplied externally through inlet 70 positioned on the rear side of unit 30 shown in FIG. 7. The light is turned on for the user-programmed time and the pressure is maintained until the set light time has elapsed. At the end of the cycle, the light turns off, pressure is released, and the pressure sealing mechanism retracts.

The "purge" mode is a curing cycle that purges the atmosphere prior to curing the work piece under pressure and light. When used with nitrogen or argon, no tacky surface will be observed (i.e., oxygen is removed). This mode is usually used for the application of the final layer of material. After the work is placed in the curing chamber and the chamber is closed, the pressure chamber is automatically pressure sealed after the start key is pressed. The chamber is then pressurized and exhausted up to about three or four times before being maintained at the desired pressure. The chamber will remain pressurized for the remainder of the user programmed pressure time, and then the light will turn on (still pressurized) until the light time has elapsed. At the end of the cycle the light turns off, pressure is released and the pressure sealing mechanism retracts. The time for maintaining pressure may be from about 1 minute to about ten minutes. A typical curing cycle is usually in the range from about 2 minutes to about 5 minutes. The pressure does not typically go above about 85 psi.

When a cycle is being performed, the times for light and pressure will remain set until changed, or until the power is turned off. A Start light emitting diode (LED) will indicate that a cycle is running. A Stop LED will indicate when there is no cycle running. The time display counts down in minutes and seconds for each segment, i.e., the initial pressure time (if required) will count down from set time to 0:00, followed by a light curing cycle that will count down from set time to 0:00. If a purge is used, it is included in the pressure time. Cover 32 is interlocked under pressure. The locking device is comprised of pins or segments 33 that lock into latches 35 as shown in FIG. 4. Dome 41 shown in FIG. 5 is locked and sealed in this manner for a pressurized operation. To open latches 35, pressure is released, the latches are rotated in the reverse direction, allowing the unit to be opened.

Figure 6:
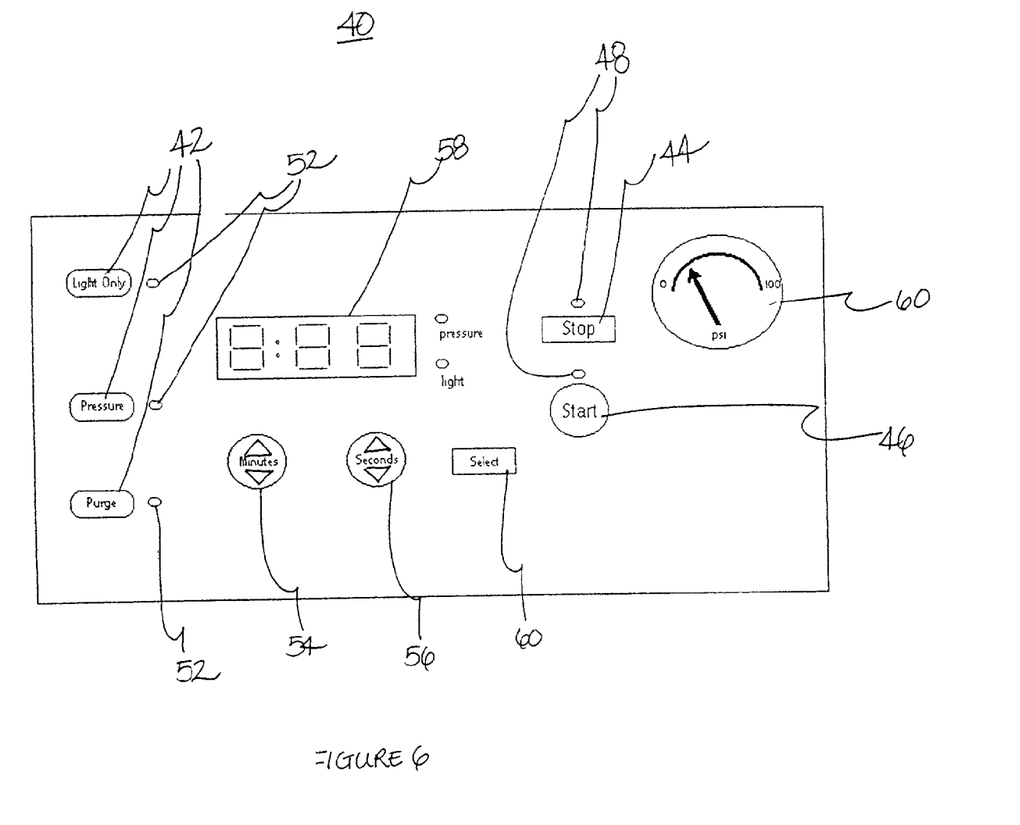
FIG. 6 is a perspective view of the front panel on the apparatus shown in FIG. 2.

FIG. 6 shows a control panel 40 located on the front of base 38. Panel 40 includes a series of buttons 42 that are labeled with the appropriate word to describe the curing mode to be actuated. Buttons 44 and 46 are labeled Stop and Start, respectively, and are used to stop and start the procedure. Panel 40 includes a time display 58 and a pressure gauge 60. Running a cycle involves placing a work piece on platform 36 and closing and securing cover 32. The mode of operation, such as for example, by pressure, is selected by pressing the Pressure key. The LED buttons 52 will indicate if the mode has been selected. If the Pressure mode is selected, the LEDs located next to Light Only and Pressure will be lit. Buttons 54 and 56 labeled Minutes and Seconds, respectively, can be pressed to reach the desired time for the mode. The Select button 60 is used to select the pressure or light mode for input of time. LED buttons 48 located above the Stop and Start buttons indicate when a cycle is running (Start LED is lit) and when a cycle is over (Stop LED is lit).

A curing operation using the pressure and light mode proceeds as follows. Press Start key 46 to start the cycle. The pressure latches 35 will close and seal the chamber. The Start LED will light to indicate the cycle is in progress. The unit will first pressurize the chamber to up to about 85 psi. Pressure is set by an external regulator. The time display will begin to count down in seconds. After the pressure segment, the Light will be activated. The Pressure LED will go out and the Light LED will go on indicating that the time display is now counting down for the time that the light is on. Pressure will be maintained. The time display will continue to decrease until the time reaches 0:00. The pressure will then be released. When the pressure reaches nominal pressure, the Stop LED will come on and the Start LED will go out. Pressure latches 35 will then retreat.

To add a purge segment to the cycle, the Purge key or button is pressed when setting up the mode. To begin the cycle, the Start key is pressed. The Start LED will light to indicate that the cycle is in progress. Pressure latches 35 will engage. The unit will first pressurize chamber 31. The time display will begin to count down from programmed pressure time. The purge time is included in the pressure time. Only the Pressure LED above the time display indicates that the time is for the pressure segment. The unit will purge the chamber and then pressurize it. The purge cycle includes two or more segments comprising the application of pressure followed by a release of pressure. Pressure is then applied and maintained. After the pressure segment, the curing light will be activated. The Pressure LED will go out and the Light LED will go on indicating that the time display is now counting down the Light time. Pressure will be maintained. The time display will continue to decrease until the time reaches 0:00. The pressure will then be released and a timed delay will begin to allow venting of pressure. When the pressure reaches nominal pressure, the pressure latches will automatically retract, the Stop LED will come on and the Start LED will go out.

A light only cycle can be activated by selecting only the light mode button and proceeding with the time. The Light LED will turn on and the time display will decrease until the time reaches 0:00. The Stop LED will come on and the Start LED will go out.

The unit is supplied with an external air or gas source that is switched using pressure valves. The internal line into the pressure chamber has a small restriction orifice that limits the flow of air or gas into the pressure chamber. The pressurized system also has a pressure relief valve. The relief valve will open at a maximum pressure level and limit the pressure to the pressure chamber. The air or gas flow through the pressure relief valve is greater than the input restrictor orifice, which also limits the pressure of the chamber to safe levels in the event of the input line exceeding maximum levels. The air or gas is exhausted by a pressure release valve and the pressure level is monitored by a pressure switch or transducer. When the pressure has been released and falls to a safe level the automatic latching mechanism will release the pressure seal in such a way as to prevent the top pressure dome from flying open in the event that the pressure measuring function failed and pressure was still in the pressure chamber. The front panel pressure gauge will also indicate the internal pressure level.

Figure 8:
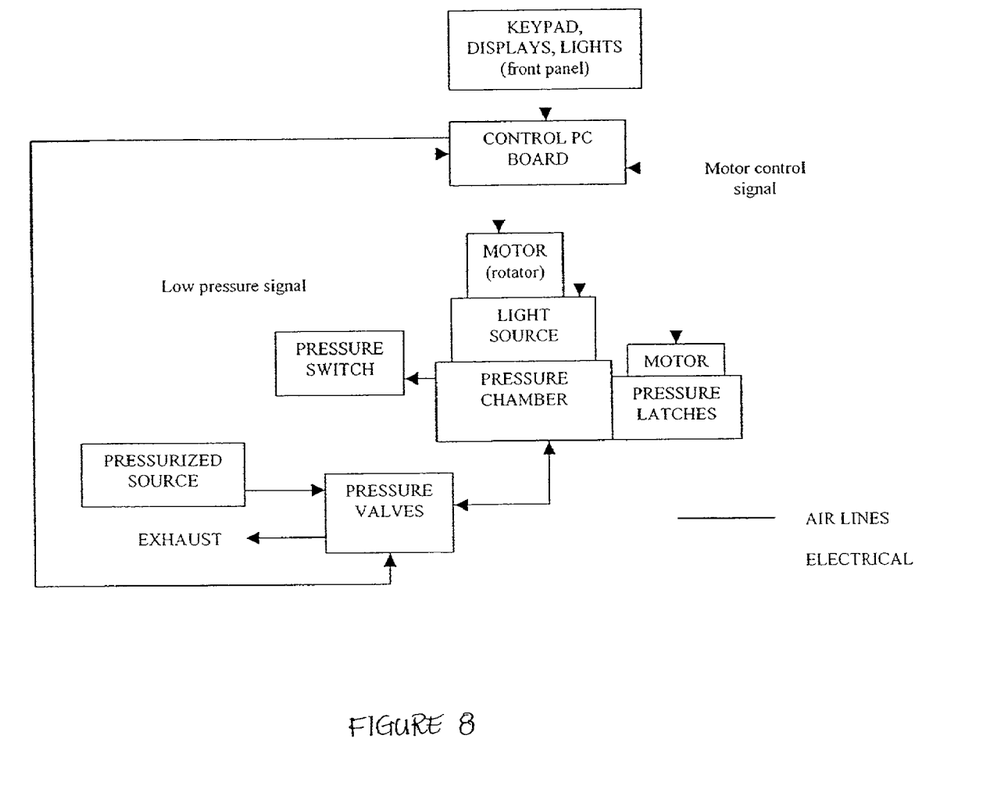
FIG. 8 is a block diagram showing the electrical connections and air line connections.

FIG. 8 is provided to show the electrical connections and air or gas line layout. The front panel 40 is the control panel that is operatively associated with a processing device located internally. The control panel receives input from an operator relating to the light source and the gas source. The processing device is operatively associated with the light source and the gas source for controlling curing of the dental material by light and pressure within the air-tight chamber. The processing device may include, but is not limited to, a microprocessor, a microcontroller, a microcomputer, a controller, a digital signal processor, a central processing unit (CPU), or an application specific integrated circuit (ASIC). The processing device may be configured to cause gas to supply gas under pressure to the air-tight chamber prior to the time the light source supplies light to the chamber. It may be further configured to cause gas pressure to be maintained in the chamber at a constant level during the time the light source supplies light to the chamber. The processing device may be configured to cause the gas pressure to be initially supplied and subsequently released at least twice in succession, followed by application of pressure, whereby gas pressure is maintained at a constant level with in the chamber during the time the light source supplies light to the chamber.

While preferred embodiments have been shown and described, various modifications and substitutions may be made thereto without departing from the spirit and scope of the invention. Accordingly, it is understood that the present invention has been described by way of illustration and not limitation.

What is claimed is:

1. An automated apparatus for curing a ploymerizable dental material by light and pressure comprising:
   an air-tight chamber for receiving the dental material therein;
   a light source for supplying light to an interior of the air-tight chamber, wherein the light source comprises tungsten, halogen, mercury vapor, short arc xenon or a metal halide source;
   a gas inlet for receiving pressurized gas into he interior of the air-tight chamber from an independent gas source;
   a processing means operatively associated with the light source and the gas source for controlling curing of the dental material by light and pressure within the air-tight chamber;
   a control means operatively associated with the processing means for receiving input from an operator relating to operation of the light source and the gas source;
   latch means for pressure sealing the air-tight chamber;
   means for retracting the latch means after the pressure in the air-tight chamber has reached a nominal pressure value;
   a control panel having a Start button and a Stop button for starting and stopping the apparatus; and
   whereby the air-tight chamber is automatically pressure sealed after the Start button is pressed.

2. The apparatus of claim 1 wherein the processing means includes at least one of a microprocessor, microcontroller, a microcomputer, a controller, a digital signal processor, a CPU and an Application Specific Integrated Circuit (ASIC).

3. The apparatus of claim 1 wherein the processing means comprises a means for causing the gas source to supply gas under pressure to the chamber prior to the time the light source supplies light to the chamber.

4. The apparatus of claim 3 wherein the processing means comprises a means for causing gas pressure to be maintained in the chamber at a constant level during the time the light source supplies light to the chamber.

5. The apparatus of claim 1 wherein the processing means comprises a means for causing the gas pressure to be initially supplied and subsequently released at least twice i succession, followed by application of pressure, whereby the gas pressure is maintained at a constant level within the chamber during the time the light source supplies light to the chamber.

6. The apparatus of claim 1 wherein the air-tight chamber includes a base and a movable cover.

7. The apparatus of claim 6 wherein the movable cover includes segments configured to engage safety latches positioned on the base.

8. The apparatus of claim 1 wherein the gas source is a source of air.

9. The apparatus of claim 1 wherein the gas source comprises nitrogen.

10. The apparatus of claim 1 wherein the gas source comprises an inert gas.

11. The apparatus of claim 1 wherein the inert gas comprises argon, xenon, krypton or a mixture thereof.

12. The apparatus of claim 1 wherein the source includes at least one lamp.

13. The apparatus of claim 1 wherein the control means comprises a pressure gauge, a time display, and a series of controls for inputting instructions to the processing means.

14. An automated apparatus for curing a ploymerizable dental material by light and pressure comprising:
   an air-tight chamber for receiving the dental material therein;
   a light source for supplying light to a interior of the air-tight chamber, wherein the light source comprises tungsten, halogen, mercury vapor, short arc xenon or a metal halide source;
   a gas inlet for receiving pressurized gas into the interior of the air-tight chamber from an independent gas source;
   a processing device operatively associated with the light source and the gas source for controlling curing of the dental material by light and pressure within the air-tight chamber;
   retractable pressure latches for sealing the air-tight chamber;
   a motor for retracting the pressure latches after the air-tight chamber has vented;
   a control panel operatively associated with the processing means for receiving input from an operator relating to operation of the light source and the gas source;
   a control panel having a Start button ad a Stop button for starting ad stopping the apparatus; and
   whereby the air-tight chamber is automatically pressure sealed after the Start button is pressed.

15. The apparatus of claim 14 wherein the processing device includes at least one of a microprocessor, microcontroller, a microcomputer, a controller, a digital signal processor, a CPU and an Application Specific Integrated Circuit (ASIC).

16. The apparatus of claim 14 wherein the processing device comprises a means for causing the gas source to supply gas under pressure to the chamber prior to the time the light source supplies light to the chamber.

17. The apparatus of claim 14 wherein the processing device comprises a means for causing the gas pressure to be maintained in the chamber at a constant level during the time the light source supplies light to the chamber.

18. The apparatus of claim 14 wherein the processing device comprises a means for causing the gas pressure to be initially supplied and subsequently released at least twice in succession, followed by application of pressure, whereby the gas pressure is maintained at a constant level within the chamber during the time the light source supplies light to the chamber.

19. The apparatus of claim 14 wherein the air-tight chamber includes a base and a movable cover.

20. The apparatus of claim 19 wherein the movable cover includes segments configured to engage safety latches positioned on the base.

21. The apparatus of claim 14 wherein the gas source is a source of air.

22. The apparatus of claim 14 wherein the gas source comprises nitrogen.

23. The apparatus of claim 14 wherein the gas source comprises an inert gas.

24. The apparatus of claim 23 wherein the inert gas comprises argon, xenon, krypton or a mixture thereof.

25. The apparatus of claim 14 wherein the light source includes at least one lamp.

26. The apparatus of claim 14 wherein the control panel comprises a pressure gauge, a time delay, and a series of controls for inputting instructions to the processing means.

27. The apparatus of claim 14 further comprising one or more fans to prevent overheating of the dental material.

28. The apparatus of claim 1 further comprising one or more fans to prevent overheating of the dental material.

* * * * *